United States Patent [19]

Stroetmann

[11] 4,427,651
[45] Jan. 24, 1984

[54] ENRICHED PLASMA DERIVATIVE FOR ENHANCEMENT OF WOUND CLOSURE AND COVERAGE

[75] Inventor: Michael Stroetmann, Münster, Fed. Rep. of Germany

[73] Assignee: Serapharm Michael Stroetmann, Münster, Fed. Rep. of Germany

[21] Appl. No.: 385,665

[22] Filed: Jun. 7, 1982

[30] Foreign Application Priority Data

Jun. 25, 1981 [DE] Fed. Rep. of Germany ....... 3124962

[51] Int. Cl.³ .................... A61K 9/14; A61K 35/14; A61K 37/00
[52] U.S. Cl. ........................................ 424/46; 424/45; 424/101; 424/177
[58] Field of Search ................. 424/101, 177, 46, 45

[56] References Cited

U.S. PATENT DOCUMENTS 4,298,598 11/1981 Schwarz et al. .................... 424/101
4,362,567 12/1982 Schwarz et al. .................... 424/101

OTHER PUBLICATIONS

Schwarz et al.—Chem. Abst., vol. 94 (1981), p. 36318q.
Schwarz et al.—Chem. Abst., vol. 94, (1981), p. 36384h.
McKendrick et al.—Chem. Abst., vol. 76 (1972), p. 17809n.

Primary Examiner—Sam Rosen
Attorney, Agent, or Firm—Gordon W. Hueschen

[57] ABSTRACT

A sprayable preparation for accelerated hemostasis and optimized biochemical control of wound closure contains a powdery mixture of 15 to 60% by weight of thrombin, 5 to 80% by weight of a desiccating and stabilizing agent, viz., albumin, globulin and/or fibrinogen, and 1 to 10% by weight of a fibrinolysis inhibitor. The powdery mixture is suspended in a low-boiling, anhydrous solvent, which is used as a propellant. For effective wound closure and coverage, a spray jet of this suspension is directed onto the wound under evaporation of the solvent so that substantially only the dry, solid powdery mixture reaches the wound. This method of application by spraying is also disclosed.

20 Claims, No Drawings

ENRICHED PLASMA DERIVATIVE FOR ENHANCEMENT OF WOUND CLOSURE AND COVERAGE

The present invention relates to an enriched plasma derivative in the form of a biochemical substrate for accelerated hemostasis and optimum control of wound closure. In particular, the invention relates to such a plasma derivative for enhancement of wound closure and coverage based on human plasma derivatives containing thrombin and a fibrinolysis inhibitor.

It is the task of the blood coagulation system to form insoluble fibrin from certain plasma components, in particular from dissolved fibrinogen, and to deposit the same on the wound in order to stop bleeding chemically and mechanically. In the course of this hemostasis, fibrin forms a mechanically-resistant closure of tissue and vascular injuries. On the other hand, together with the fibrinolytic system and the components of the coagulation system, fibrin constitutes the basis of the cellular "repair" of tissue damage.

As has been shown by research results in the past ten years, the biochemical control of wound closure is a multi-stage catalytic process involving a multiplicity of forward and backward reactions or couplings, wherein a controlled coordination of the blood coagulation factors takes place, of which so far at least thirteen have been recognized and characterized. The coagulation itself is improved intravascularly by the endothelium. Additionally, the factors of the thrombocytes are of a particular importance.

The analytical clarification of the mechanisms of blood coagulation, the isolation of the factors and substances participating in the blood coagulation, the use of suitable supplementary materials and the development of suitable methods of application, offer to medical wound treatment the chance of an acceleration of hemostasis as well as of optimum control of wound closure. In particular, it has become possible to separate from natural plasma certain preparations, to store them and, when required, to apply them onto the wound together with further substances necessary for fibrin formation and interlacing in order to achieve controlled hemostasis.

In the art, a typical system of this kind is known by the term "fibrin adhesive." Therein, first a fibrinogen solution is applied onto the tissue parts to be adapted. Thereafter, small amounts of a highly concentrated thrombin and factor-XIII solution are dropped thereon for coagulation. A fibrinolysis inhibitor is added locally in order to prevent a premature lysis and thus the premature dehiscence of the adapted tissue parts. This technique causes great expenditure and is complicated due to the separate preparation, storage and application of the mentioned substances. Moreover, only a restricted spectrum of means (fibrinogen, thrombin, factor XIII, fibrinolysis inhibitor) is applied to the profile of requirements, viz, accelerated hemostasis and optimum wound closure.

In practice, the deep-frozen fibrinogen solution is thawed, thrombin and calcium chloride are added thereto, the mixture is kept for some time till the commencement of the polymerization reaction becomes noticeable by an increase of the viscosity, and thereupon this reaction mixture is applied onto the tissue parts to be joined. In many cases, the expenditure for preparing the "fibrin adhesive" suitable for use and the short life of the preparation ready for use have proven to be an impediment. E.g., the application is difficult for the practising physician because he cannot reliably determine the short-time interval of a still liquid adhesive suitable for use. Difficulties will arise from the limited life of a "fibrin adhesive" ready for use, especially if extensive coverage of heavily bleeding wounds, possibly even in poorly-accessible body cavities, is required.

On the basis thereof, it is an object of the present invention to provide an enriched plasma derivative for supporting wound closure and coverage which has practically unlimited storage stability at room temperature, is directly and without the addition of other necessary components applicable onto the wound and the area of operation, respectively, and which is excellently suited for use in poorly-accessible body cavities and/or for extensive coverage of heavily bleeding wounds, as well as its method of use.

According to the present invention this object is solved by an enriched plasma derivative in the form of a biochemical substrate for accelerated hemostasis and optimum control of wound closure, whose composition is selected with regard to an optimized activation of the exogenic and/or endogenic coagulation system and under consideration of a multiplicity of physiological and, if applicable, pathological aspects, whose constitutents exclusively are provided in powdery state and which is prepared in the form of a spray. Preferably, the main constituents of the powdery plasma derivative include fibrinogen, thrombin, components of the prothrombin complex, and protease inhibitors. Furthermore, additionally admixtures of blood platelet extracts, antibiotics, and the like may be provided.

In particular, the present invention provides for the solution of the above-specified object an enriched plasma derivative for enhancement of wound closure and coverage based on human plasma derivatives containing thrombin and a fibrinolysis inhibitor, in which in a low-boiling, anhydrous solvent, which is used as a propellant, a powdery mixture containing 15 to 60% by weight of thrombin, 5 to 80% by weight of a desiccating and stabilizing agent, viz., albumin, globulin and/or fibrinogen, and 1 to 10% by weight of a fibrinolysis inhibitor (the specified percentages are respectively based on the total weight of the powdery mixture) is suspended, and for wound closure and coverage, respectively, a spray jet of this suspension is directed onto the wound under evaporation of the solvent so that substantially only the dry, solid powdery mixture reaches the wound. The method of use also comprises a part of the present invention.

Advantageous modifications and further embodiments of the present invention are apparent from the subclaims. These relate, above all, to further additives to the powdery mixture such as prothrombin, powdery collagen, platelet concentrate, factors for hemophilic treatment and antibiotics and, furthermore, the selection of the solvents used as the propellant.

In contrast to the "fibrin adhesives" common so far, the present invention is based on the experience that, for the enhancement of wound closure and coverage, the employment of additional fibrinogen is not required in any case, and that the thrombin, which, as is well known, is rather sensitive, at room temperature has substantially unlimited storage stability in solid, dry, powdery state when mixed with selected fine, dry, powdery desiccating and stabilizing agents, without there being a substantial decrease of its biochemical activity.

Even if the powdery mixture contains as the desiccating and stabilizing agent solid, dry, powdery fibrinogen, there will be no fibrin formation or any appreciable decrease of the activity of the coagulation enzymes even after long-time storage due to the solid state of all components of the powdery mixture and the absence of water. The additional presence of prothrombin further increases the storage stability, in particular at moderately increased temperatures of not more than approx. 40° C. However, on the other hand, the biological activity, in the tissue sealing as well as the conversion into a hemostatic fibrin wound coating, set in within a short period of time after partial passing into solution and dissolution of the dry powdery mixture in the body fluid. Very quickly, e.g., after 2 min., there occurs an accelerated hemostasis. The biochemical control of the wound closure is increased and optimized by the increased offer of coagulation enzymes, above all, thrombin and, where applicable, prothrombin. The adding of a fibrinolysis inhibitor prevents the re-dissolution of the already formed fibrin clot. The adding of platelet factors stimulates the coagulation of the escaping blood, the contained growth factors optimize the wound treatment. The collagen possibly also added absorbs the fibrin clot and increases the adhesion of the wound closing material.

On the basis of the realization that the required factors when dryly mixed with each other are storable at room temperature without any appreciable loss of activity, it was recognized according to a further aspect of the invention that this dry powdery mixture may be sprayed with a suitable propellant which does not partially pass the powdery mixture into solution so that the application of the material in poorly accessible body cavities and/or the extensive covering of heavily bleeding wounds becomes possible within a short time. The prerequisite is an absolutely anhydrous solvent so as to preclude an activation of the components of the powdery mixture during storage. In the case of application of a low-boiling propellant such as, e.g., "Frigen 114"® (1,2-dichloro-1,1,2,2-tetrafluoroethane), it is achieved that practically the entire propellant evaporates during the spraying step so that substantially only the dry, solid powdery mixture reaches the wound.

Thus, the present invention provides a wound closure and covering material which has practically unlimited storage stability at room temperature, which is directly and without addition of other necessary components applicable onto the wound and area of operation, respectively, and which is excellently suited for use in poorly accessible body cavities and/or the extensive covering of heavily bleeding wounds. The dry, solid powdery mixture reaching the wound absorbs liquid, dries the wound area, causes the blood to coagulate and advances the healing of the wound. Therefore, the preparation is excellently suited for the treatment of heavily discharging wounds and/or chronically ulcerating wounds. The suitability for the hemophilic treatment can additionally be improved by the adding of factors VIII and/or IX.

Particularly preferred fields of application of the wound closing and covering material according to the present invention are plastic surgery for sealing and suturing skin flaps, operative dentistry, e.g., for closing cavities, ear, nose and throat operations, mamma surgery for fixing skin flaps and tissue parts, use in hypogastric region, in the vaginal region and other poorly accessible body cavities.

In the following, the invention will be explained in detail with reference to preferred embodiments.

The dry, solid powdery mixture sprayed with the spray jet must contain at least thrombin, a fibrinolysis inhibitor, and a desiccating and stabilizing agent, viz, at least one constituent of the group of plasma derivatives comprising albumin, globulin and fibrinogen.

Biologically active thrombin is used as a starting substance for the fibrin formation and reduces the reaction time of the fibrinogen conversion in the escaping blood. Biologically active thrombin in the sense of this application is a thrombin the activity of which, under known, standardized conditions, amounts to at least 1,000 international units per mg of thrombin. Suitable preparations are available commercially. E.g., it is possible to obtain a suitable thrombin in microcrystalline form with a biological activity of at least 3,000 units per mg of thrombin under the trade name "Topostasin" from Hoffmann LaRoche, Grenzach, Baden.

According to an important aspect of the invention, an exceptionally high thrombin availability is provided. Therefore, the content of thrombin in the powdery mixture shall be at least 15% by weight. The upper limit of the content of thrombin depends on the efficiency of the desiccating and stabilizing agent and may be up to 60% by weight. Good results have been achieved with a thrombin content of 20 to 50% by weight; what is particularly preferred is a thrombin content of the dry powdery mixture of approx. 40 to 45% by weight.

Part of the thrombin may be replaced by prothrombin. The coagulation enzyme thrombin is sensitive and its biological activity decreases with long-time storage, whereas prothrombin constitutes a stable thrombin reserve with long-time storage stability, which in the case of access of moisture is activated by thrombin which is present and/or the flow of blood.

The solid powdery mixture may contain 0.1 to 2 parts by weight of prothrombin per 1 part by weight of thrombin. Preferably, 0.5 to 0.9 parts by weight of prothrombin are provided per 1 part per weight of thrombin. A relatively high content of prothrombin is expedient since mostly prothrombin is present in a complex of factors which contains further coagulation enzymes so that a high content of prothrombin also means a high proportion of these coagulation enzymes, which, in its turn, accelerates the blood coagulation. Therefore, the content of prothrombin may amount to 5 to 40% by weight, preferably to 20 to 35% by weight. Prothrombin may be separated from purchasable prothrombin complex or may be extracted from the plasma by barium sulphate and be recovered from the crystalline precipitate. Additionally, prothrombin is also available commercially, e.g., as "PPSB" preparation from the company Imuno AG, Vienna. Such prothrombin preparations as are convertible into thrombin to an extent of at least 95% when introduced into body fluid are well suitable.

As a further necessary component the dry, solid powdery mixture contains 1 to 10% by weight, preferably 2 to 6% by weight, of a fibrinolysis inhibitor. Suitable fibrinolysis inhibitors are known. Preferably, one or several antiplasmins are used as the fibrinolysis inhibitor. Suitable antiplasmins, e.g., are aprothenin, $\alpha_1$-antiplasmin and/or trypsin inhibitor. A 1:1 mixture of $\alpha_1$-antiplasmin and $\alpha_2$-macroglobulin is also well suited. The adding of such antiplasmins prevents the re-dissolution of already formed fibrin clots. According to one example of a process for obtaining suitable $\alpha_1$-antiplasmin, fibrinogen is covalently bonded to "Sepharose"* and converted into fibrin by thrombin. The fibrin thus immobilized serves as receptor for the plasmatic antiplasmin, which is bonded upon passage of plasma through the column and may be washed with ε-aminocaproic acid.

* TM, sepharose is agarose namely a linear polysaccharide of α-galactose and 3'6-anhydro-L-galactose.

Furthermore, the dry, solid powdery mixture contains at least a desiccating and stabilizing agent. It is the task of this desiccating and stabilizing agent to ensure the sprayability and the storage stability of the solid thrombin without any appreciable loss of activity in the presence of a propellant. As the desiccating and stabilizing agent at least one of the plasma derivatives, namely albumin or globulin or fibrinogen, is provided. In contrast to the known proposals, the wound closing and covering material according to the invention need not necessarily contain fibrinogen since a satisfactory hemostatic and wound closing effect is ensured already by the high thrombin content, increased, where appropriate, by the presence of prothrombin. E.g., the material made of the mentioned plasma derivatives, which is provided by the invention, may contain only albumin, which then mainly acts as a desiccating and stabilizing agent and ensures the storage stability, biological activity and sprayability of the solid, powdery thrombin. Such solid, microcrystalline albumin is commercially available and can, e.g., be obtained from the company Behring-Werke, Marburg.

Alternatively, it is possible to provide as plasma derivative only globulin. Preferably, the commercially available mixture of α, β- and γ-globulin, e.g., sold by Böhringer, Mannheim, is used.

A further desiccating and stabilizing agent coming into consideration is fibrinogen obtained from human plasma. Suitable preparations are also commercially available, e.g., from Behring-Werke, Marburg.

Furthermore, a well suitable fibrinogen may be obtained from human plasma by precipitation with a mixed solvent containing glycine, β-alanine and ethanol and subsequent dialysis and lyophilization of the precipitate. Such microcrystalline fibrinogen has a molecular weight of 340,000±5%, is slightly partially digested in the α-chain, dissolves rapidly after introduction into body fluid, wherein the proportion of fibrinogen clottable in solution shall amount to at least 85%, and immediately thereafter, e.g., in less than 2 min., starts to polymerize. 10 parts by weight of such fibrinogen contain less than 0.1 part by weight of cryo-insoluble globulin. It has been found that the fibrin polymerization takes place the more rapidly, the less cryo-insoluble globulin is present. As far as the fibrinogen, which is not only used as a desiccating and stabilizing agent for the thrombin, but is also provided to increase the fibrinogen availability in the area of the wound, such fibrinogen depleted of cryo-insoluble globulin is preferably used for this reason.

Instead of a single component, it is possible to provide as the desiccating and stabilizing agent also a mixture of two or more components of the group comprising albumin, globulin and fibrinogen. E.g., a mixture of albumin and fibrinogen has proven to be successful.

The total of the amounts of albumin, globulin and/or fibrinogen may amount to 5 to 80% of the weight of the dry, solid powdery mixture. Preferably, a proportion of approx. 8 to 70% by weight is provided.

Furthermore, the solid powdery mixture may contain solid, powdery, water-soluble collagen. Suitable collagen has been obtained from tendons or skin, has an average molecular weight of approx. 3 to 5 million the powdery collagen is water-soluble to at least 90%.

The collagen blown onto the wound as a constituent of the powdery mixture absorbs liquid and activates the thrombocytes carried along with the escaping blood, and thus accelerates blood coagulation. Furthermore, collagen increases the viscosity in the area of the wound and facilitates the adhesion of the wound closing material to the tissue parts. According to a preferred embodiment of the invention, the solid powdery mixture shall additionally contain collagen. The amount of collagen is not critical and may approximately range from 2 to 24% of the weight of the powder.

If the powdery mixture contains collagen, the proportion of desiccating and stabilizing agent, viz, of the plasma derivatives albumin, globulin and/or fibrinogen, may be reduced. In this case, a proportion of approx. 3 to 12% by weight of collagen and 8 to 70% by weight for the total of the proportions of albumin, globulin and/or fibrinogen has proven to be a success.

Furthermore, the solid powdery mixture may additionally contain platelet extract. The platelets belong to the cellular constituents of the blood. They are separated from the erythrocytes as a "buffy coat" by centrifugation. This cell fraction is washed with saccharine solutions, wherein it is liberated from erythrocytes still admixed therewith. The membranes of the cells are liberated by suitable cellysis and separated from the cell sap by centrifugation. The cell walls of the platelets contain phospholipid-protein structures, which are used both for activating the endogenic coagulation cascade and for orienting the enzymes participating in the coagulation. After drying of the membrane particles, homogenization and extraction, a product is obtained therefrom which is soluble and reactive under physiological conditions.

In view of the high activity, a low proportion of platelet extract is sufficient, e.g., approx. from 0.2 to 2% of the weight of the powdery mixture; preferably, the proportion of platelet extract amounts to 0.5 to 1.2% by weight.

By way of example, a platelet extract is obtained as follows:

"Buffy coat" of a sediment from human full blood is exhaustively washed with Seiler solution (glucose-salt mixture) for separating the erythrocytes. The thus prepared leucocyte-monocyte-thrombocyte preparation is dissolved by adding Triton X ®*, the insoluble portion is centrifuged off and the supernatant solution is fractionally precipitated with saturated ammonia sulphate at a pH of 7.4. The sediment is centrifuged off, dialyzed and dried. The phospholipid content of the fraction amounts to approx. 16 to 25%. When examined in the thromboplasmin test, the preparation proves to be coagulation-active. The growth increase is examined by fibroblast increase in the culture.

*polyethylene glycol p-isooctylphenyl ether surface active agent.

In addition to the above-mentioned necessary and optionally provided components of the powdery mixture, this mixture may contain further, known factors and substances having an effect on the blood coagulation and influencing the healing of wounds, all of them in solid, powdery form. Furthermore, the solid powdery mixture may additionally be enriched with bactericides and/or antibiotics and/or may contain other additives effective in combating certain pathological conditions; inter al., these include, e.g., penicillins, aureomycins, streptomycins and the like, furthermore, antihistamines, vasopressins and, moreover, the coagulation factors VIII and/or IX for hemophilic wound healing. The proportion of the mentioned antibiotics may amount to approx. 10,000 to 50,000 units per 1 g of powdery mixture. The proportion of the coagulation factors VIII and/or IX may amount to approx. 1 to 10 units per 1 g of powdery mixture. The presence of these factors VIII and/or IX, which are important for hemophilic treatment, is capable not only of closing the wound but even activates the endogenous blood to close the wound. Furthermore, salts promoting the activation of the coagulation enzymes, such as, e.g., $CaCl_2$, may be provided.

A preferred embodiment of the invention provides for the solid powdery mixture to be sprayed. In the following composition, the percentages specified are based on the total weight of the powdery mixture.

| | |
|---|---|
| 20 to 50 | % by weight of thrombin |
| 5 to 40 | % by weight of prothrombin |
| 8 to 70 | % by weight of albumin, globulin and/or fibrinogen |
| 2 to 6 | % by weight of fibrinolysis inhibitor |
| 3 to 12 | % by weight of water-soluble collagen |
| 0.5 to 1.2 | % by weight of platelet extract |

In addition, the powdery mixture may contain 10,000 to 50,000 units of antibiotics per 1 g of powdery mixture, and
1 to 10 units of factor VIII and/or IX per 1 g of powdery mixture.

All of the above-mentioned preparations are solid at room temperature and at temperatures of up to 56° C. and substantially microcrystalline. The solid powdery mixture is obtained from these components by simple, dry mixing. E.g., the mixing may be carried out by treatment in a ball mill for 10 min. Alternatively, the mixing may be carried out by ultrasonic treatment and sieve classification. In each case, a dry, freely flowing powder is obtained from the homogeneous mixture of the constituents.

For ensuring a good sprayability, the average particle size of the powdery mixture preferably is between approx. 0.1 μm and approx. 5 μm. In the case of even finer powders, there will be the risk of agglomeration and clogging. Coarser powders cannot sufficiently be sprayed and their dissolution in the body fluid is delayed. In connection with conventional spray heads which, e.g., have a diameter of 5 μm, an average particle size of the powdery mixture of approx. 0.5 to 2 μm has proven to be a success; in this case, an average particle size of the powder mixture of approx. 1 to 1.5 μm is preferred particularly. For ensuring this particle size, the powder is ground to sufficient fineness and the ground product is sieve-classified.

In order to provide a sprayable wound closing and covering material, the solid powdery mixture of the above-mentioned components is suspended in a low-boiling, anhydrous solvent, which is used as a propellant. A suitable low-boiling solvent will be provided if the solvent, after leaving the spray nozzle, evaporates completely before reaching the surface of the wound. Thereby one achieves, even in the case of use of physiologically inert and harmless solvents, that upon spraying substantially only the dry, solid powdery mixture reaches the wound, whereas the content of solvent, provided it reaches the wound at all, remains below the detection limit of specific effects. In order to ensure a sufficiently rapid evaporation, the boiling point of the solvent shall be below 10° C. at atmospheric pressure (approx. 100 kPa). Solvents which are well suited for the purpose according to the invention and which are liquid at room temperature only at increased pressure are individual selected halogenated hydrocarbons or an azeotrope of such hydrocarbons, as known by the technical term "Frigens"®. E.g., "Frigen 114" (tetrafluorodichloroethane $C_2F_4Cl_2$, boiling point 4.1° C.), or "Frigen 13" (chlorotrifluoromethane $CF_3Cl$, boiling point $-81.4°$ C.), or "Frigen 12" (difluorodichloromethane $CF_2Cl_2$, boiling point $-30.0°$ C.) are well suited. In the case of use of such Frigens as a propellant, preferably 3 to 6 parts by weight of Frigen propellant are used per 1 part by weight of the powdery mixture. In addition, liquefied gases such as, e.g., liquid carbon dioxide, liquid nitrogen, liquid methane, liquid laughing gas (nitrous oxide $N_2O$) or the like come into consideration as a propellant. In individual cases, it is also possible to provide low-boiling mixtures of organic solvents such as, e.g., acetone/alcohol mixtures or acetone/ether mixtures (e.g., 8 parts by volume of acetone per 2 parts by volume of ether). In addition to their own vapor pressure, the spraying of such low-boiling organic solvents advantageously is also supported by a mechanical reduction of volume of the interior of the container, e.g., through a mechanically or spring-operated pressure plunger, a pneumatically operated diaphragm, or the like.

It is important that the low-boiling solvent provided as a propellant is anhydrous so as reliably to exclude an activation of the coagulation enzymes and of the possibly provided fibrinogen in the course of storage. The moisture content of the Frigens guaranteed by the manufacturers of not more than 10 mg/kg ($=0.001\%$) proves to be sufficient for the present purposes so that no additional drying measures are required.

The following table gives examples of compositions of the enriched plasma derivative for supporting wound closure and coverage.

TABLE

| Examples | I | II | III | IV | V | VI | VII | VIII |
|---|---|---|---|---|---|---|---|---|
| Components (g) | | | | | | | | |
| Thrombin | 30 | 48 | 40 | 25 | 35 | 45 | 50 | 20 |
| Prothrombin | | | 30 | 35 | 25 | 15 | 34.5 | 5.8 |
| Fibrinogen | 25 | | 25 | 15 | 29.4 | | | 30 |
| Albumin | 20 | 30 | | 5 | | 29.2 | | 15 |
| Globulin | 20 | 20 | | 5 | | | 10 | 10 |
| Collagen | | | | 10 | 5 | 7 | 3 | 12 |
| Platelet extract | | | | 1 | 0.6 | 0.8 | 0.5 | 1.2 |
| Fibrinolysis inhibitor* | 5 | 2 | 5 | 4 | 5 | 3 | 2 | 6 |
| Propellant (g) | | | | | | | | |

TABLE-continued

| Examples | I | II | III | IV | V | VI | VII | VIII |
|---|---|---|---|---|---|---|---|---|
| Frigen 114 | 400 | | | 350 | 400 | | 400 | 500 |
| Frigen 12 | | 500 | | | | 500 | | |
| Frigen 13 | | | 600 | | | | | |

*The fibrinolysis inhibitor used in all examples was "Trasylol" (TM) from Bayer AG, Leverkusen.

When the powdery and coagulation-active material according to the above examples I to VIII is sprayed at a distance of approx. 10 to 30 cm, a thin whitish film forms on the surface of the wound which is immediately dissolved by escaping blood. Within a few minutes the sprayed wound surface is sealed and closed by the blood coagualation.

Regarding the powdery mixture used in Example V, the *thrombin activity*, the fibrin linkability and the coagulation activity were tested and the following results were obtained.

The dry powdery mixture according to Example V was dissolved in a concentration of 0.5 mg of powdery mixture per 1 ml of 0.9%, aqueous NaCl solution, 100 μl samples of this solution were tested with a standard solution of a chromogenic substrate (S2222 of the company Kabivitrum, Stockholm). In the end point analysis, the extinction increase at 405 nm must correspond to a thrombin activity of at least 0.001 international units. The system is calibrated with known amounts of thrombin so that it is easily possible to determine values lying therebetween.

In the present case, it was possible to prove 0.0025 to 0.003 units. The "units" have the meaning that 1 unit must cause 1 ml of a standardized fibrinogen solution to coagulate within 15 sec.

Testing of the fibrin linkability

The fibrin clots formed by thrombin were immediately exhaustively washed in a 0.9% aqueous NaCl solution and thereupon dissolved in 0.1% monochloroacetic acid.

The extinction value at 280 nm is used as a reference value. The clots later removed from the formulation at defined time intervals are less soluble. Their extinction values are compared with the zero value. After 30 min. at 37° C. the formed fibrin is no longer detectable in the specified solvent.

Testing of the coagulation activity of the enriched plasma derivative 10 mg portions of the dry powdery mixture according to Example V were dissolved in a 5 mM $CaCl_2$ containing 0.9% aqueous NaCl solution with agitation. The coagulation activity of this solution was determined by the rate of the fibrin formation. For this purpose, samples were taken at defined time intervals and examined electrophoretically as to the proportions of fibrinogen and fibrinoligomers. Under the selected conditions, the coagulation time is 70 to 90 sec., wherein 35% of the fibrinogen are converted into fibrinmonomers. The interlacing of the fibrin filaments by the factor XIII contained in the preparation is terminated within 30 min. Thereafter, the preparation can no longer be dissolved in 0.1% monochloroacetic acid.

The thrombin activity, coagulation activity, and fibrin linkability produced by the compositions of Examples I-IV and VI-VIII are similar or substantially identical to those produced with the composition of Example V.

The biological activity in tissue sealing as well as the conversion into a hemostatic fibrin wound coating set in after the dry, powdery plasma derivative has partially passed into solution and been dissolved in body fluid. Already after a short time, e.g., after 2 min., there occurs an accelerated hemostasis. The biochemical control of the wound closure is increased and optimized by the increased availability of thrombin and fibrinolysis inhibitors. The adding of the platelet factors stimulates the coagulation of the escaping blood, the contained growth factors optimizing the healing of the wound.

Any bleeding wound supplies coagulatable material which is swept away from the borders of the wound due to the flow velocity. Coagulatable, dry wound powders locally increase the coagulation potential, absorb liquid and promote the platelet adhesion. The collagen exposed in the area of the wound adsorbs the fibrin clot and increases the adhesion of the wound closing material. Due to the dry form of application, a special storing or a mixing with thrombin after application are unnecessary. The spray form makes the sealing of skin flaps, the safe-guarding of operation sutures, or the prevention of seeping hemorrhages particularly easy.

It is to be understood that the invention is not to be limited to the exact details of operation or exact compounds, compositions, methods, or procedures shown and described, as obvious modifications and equivalents will be apparent to one skilled in the art.

I claim:

1. An enriched plasma derivative composition useful for accelerated hemostasis and optimized control of wound closure, consisting essentially of thrombin, a desiccating and stabilizing agent, and a fibrinolysis inhibitor, the constituents of the composition being in powdery state, and said composition being in the form of a sprayable admixture.

2. A plasma derivative composition as claimed in claim 1, comprising fibrinogen, thrombin, components of the prothrombin complex, and a protease inhibitor.

3. A plasma derivative composition as claimed in claim 1 or claim 2, comprising also a blood platelet extract or an antibiotic.

4. An enriched plasma derivative composition of claim 1, for enhancement of wound or operation area closure and coverage, based on human plasma derivatives containing thrombin and a fibrinolysis inhibitor, consisting essentially of a powdery admixture of the following:

15 to 60% by weight of thrombin;

5 to 80% by weight of a desiccating and stabilizing agent selected from albumin, globulin, and fibrinogen; and 1 to 10% by weight of a fibrinolysis inhibitor (respectively based on the weight of the powder) suspended in a low-boiling anhydrous solvent as propellant, said suspension being adapted to permit direction of a spray jet thereof onto a wound with concurrent evaporation of the solvent so that substantially only the dry solid powdery mixture reaches the wound or area.

5. A plasma derivative composition as claimed in claim 4, wherein a part of the thrombin is replaced by prothrombin.

6. A plasma derivative composition as claimed in claim 5, wherein the powdery mixture contains 5 to 40% by weight of prothrombin.

7. A plasma derivative composition as claimed in any of claims 4, 5, or 6, wherein the powdery mixture additionally contains 2 to 24% by weight of powdery, water-soluble collagen.

8. A plasma derivative composition as claimed in any of claims 4, 5, or 6, wherein the powdery mixture additionally contains 0.2 to 2% by weight of platelet extract.

9. A plasma derivative composition as claimed in claim 1 or 4, wherein the powdery mixture consists essentially of
20 to 50% by weight of thrombin
5 to 40% by weight of prothrombin
8 to 70% by weight of an agent selected from albumin, globulin, and fibrinogen
3 to 12% by weight of water-soluble collagen
0.5 to 1.2% by weight of platelet extract, and
2 to 6 by weight of fibrinolysis inhibitor.

10. A plasma derivative composition as claimed in any of claims 1, 4, or 9, wherein the powdery mixture additionally contains 1 to 10 units of factor VIII or factor IX per 1 g of powdery mixture.

11. A plasma derivative composition as claimed in any of claims 1, 4, or 9, wherein the powdery mixture additionally contains a bactericide or antibiotic.

12. A plasma derivative composition as claimed in any of claims 1, 4, or 9, wherein the powdery mixture has an average particle size ranging between 0.1 $\mu$m and 5 $\mu$m.

13. A plasma derivative composition as claimed in any of claims 1, 4, or 9, wherein a solvent propellant is employed and wherein the solvent used as the propellant boils below 10° C. at atmospheric pressure (100 kPa).

14. A plasma derivative composition as claimed in claim 13, wherein the solvent used as the propellant is an aliphatic halogenated hydrocarbon.

15. A plasma derivative composition as claimed in claim 14, wherein the aliphatic halogenated hydrocarbon is tetrafluorodichloro-ethane ($C_2F_4Cl_2$) or difluorodichloromethane ($CF_2Cl_2$).

16. Method of treating a wound or the area of an operation comprising the step of applying an enriched plasma derivative composition thereto, by spraying, to effect accelerated hemostasis and optimized control of wound closure, said composition consisting essentially of thrombin, a desiccating and stabilizing agent, and a fibrinolysis inhibitor, the constituents of the composition being in powdery state, and said composition being in the form of a sprayable admixture.

17. Method of claim 16, wherein the composition is a sprayable admixture according to claim 4, and wherein, due to concurrent evaporation of solvent, substantially only the dry solid mixture reaches the wound or area.

18. Method of claim 17, wherein the composition sprayed is a composition of claim 9.

19. Method of claim 17, wherein the composition sprayed is a composition of claim 14.

20. Method of claim 17, wherein the composition sprayed is a composition of claim 15.

* * * * *

UNITED STATES PATENT AND TRADEMARK OFFICE
CERTIFICATE OF CORRECTION

PATENT NO. : 4,427,651
DATED : January 24, 1984
INVENTOR(S) : Michael Stroetmann It is certified that error appears in the above—identified patent and that said Letters Patent is hereby corrected as shown below:

Col. 1, line 66; "reaction" should read -- reacting --

Col. 2, lines 26 & 27; "constitutents" should read -- constituents --

Col. 6, line 52; "ammonia" should read -- ammonium --

Col. 7, line 54; "powder" should read -- powdery --

Signed and Sealed this

Seventh Day of August 1984

[SEAL]

Attest:

GERALD J. MOSSINGHOFF

Attesting Officer    Commissioner of Patents and Trademarks